United States Patent
Kusch et al.

(10) Patent No.: US 7,130,372 B2
(45) Date of Patent: Oct. 31, 2006

(54) LINEAR ACCELERATOR WITH X-RAY IMAGING ELEMENTS MOUNTED ON CURVED SUPPORT

(75) Inventors: Jochen Klaus Kusch, Concord, CA (US); Christopher Jude Amies, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 163 days.

(21) Appl. No.: 10/864,190

(22) Filed: Jun. 8, 2004

(65) Prior Publication Data

US 2005/0281389 A1    Dec. 22, 2005

(51) Int. Cl.
  *A61N 5/10* (2006.01)
  *H05G 1/02* (2006.01)
(52) U.S. Cl. .............................. 378/65; 378/9; 378/197
(58) Field of Classification Search ................ 378/9, 378/64, 65, 68, 69, 196, 197, 198
See application file for complete search history.

(56) References Cited

U.S. PATENT DOCUMENTS

| | | | | |
|---|---|---|---|---|
| 4,716,581 A | * | 12/1987 | Barud | 378/198 |
| 5,960,054 A | * | 9/1999 | Freeman et al. | 378/4 |
| 6,031,888 A | * | 2/2000 | Ivan et al. | 378/20 |
| 6,309,102 B1 | * | 10/2001 | Stenfors | 378/197 |
| 6,842,502 B1 | * | 1/2005 | Jaffray et al. | 378/65 |
| 6,865,254 B1 | * | 3/2005 | Nafstadius | 378/65 |
| 6,888,919 B1 | * | 5/2005 | Graf | 378/65 |
| 6,914,959 B1 | * | 7/2005 | Bailey et al. | 378/65 |
| 2004/0184579 A1 | * | 9/2004 | Mihara et al. | 378/65 |
| 2005/0281387 A1 | * | 12/2005 | Kusch et al. | 378/197 |

* cited by examiner

*Primary Examiner*—Allen C. Ho

(57) ABSTRACT

A system according to some embodiments may include a treatment head to emit treatment radiation, a gantry coupled to the treatment head, an x-ray tube to emit imaging radiation, an imaging device to acquire an image based on the imaging radiation, and a C-arm coupled to the x-ray tube, the imaging device, and the gantry.

15 Claims, 5 Drawing Sheets

LINEAR ACCELERATOR WITH X-RAY IMAGING ELEMENTS MOUNTED ON CURVED SUPPORT

BACKGROUND

1. Field

The embodiments described below relate generally to radiation treatment, and more particularly to imaging systems used in conjunction with such treatment.

2. Description

According to conventional radiation treatment, a beam of treatment radiation is directed toward a tumor located within a patient. The radiation beam delivers a predetermined dose of therapeutic radiation to the tumor according to an established treatment plan. The delivered radiation kills cells of the tumor by causing ionizations within the cells.

Treatment plans are therefore designed to maximize radiation delivered to a target while minimizing radiation delivered to healthy tissue. However, a treatment plan is designed assuming that relevant portions of a patient will be in a particular position relative to a treatment device during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Due to the foregoing, treatment plans are designed under the assumption that positioning errors may occur that may result in misdelivery of radiation. Treatment plans compensate for this potential misdelivery by specifying lower doses or smaller beam shapes (e.g., beams that do not radiate edges of a tumor) than would be specified if misdelivery was not expected. Such compensation may decrease as margins of error in patient positioning decrease.

It would therefore be beneficial to provide a system and method that may increase the accuracy of patient positioning during radiation treatment. When used in conjunction with conventionally-designed treatments, more accurate positioning may reduce chances of harming healthy tissue. More accurate patient positioning may also allow the use of more aggressive treatments. Specifically, if a margin of error in patient positioning is known to be small, treatment may be designed to safely radiate a greater portion of a tumor with higher doses than in scenarios where the margin of error is larger.

Recent systems attempt to improve the accuracy of patient positioning by combining a device for emitting treatment radiation with a device for emitting radiation that is more suitable for creating images. In one example, a fixed device is provided to deliver imaging radiation perpendicularly to the direction of treatment radiation and toward a fixed imaging device. The perspective provided by a resulting image is not particularly useful in determining whether a tumor or body of interest is properly positioned with respect to the treatment head.

SUMMARY

To address at least the above problems, some embodiments provide a system, method, medium, apparatus, and means to emit first imaging radiation towards a patient disposed in a first position using an x-ray tube coupled to a first support, acquire a first image based on the imaging radiation using an imaging device coupled to the first support, emit treatment radiation towards the patient disposed in the first position using a treatment head, and move the first support with respect to a second support to either transport the x-ray tube toward the second support and the imaging device away from the second support or to transport the x-ray tube away from the second support and the imaging device toward the second support. Some embodiments further include movement of the first support to rotate the x-ray tube and the imaging device around a patient isocenter, wherein emission of the treatment radiation includes emission of the treatment radiation toward the patient isocenter.

According to some embodiments, provided are a treatment head to emit treatment radiation towards a patient disposed in a first position, an x-ray tube to emit imaging radiation towards the patient disposed in the first position, an imaging device to acquire an image based on the imaging radiation, a first support coupled to the x-ray tube and the imaging device, and a second support coupled to the first support. The first support may be movable with respect to the second support to either transport the x-ray tube toward the second support and the imaging device away from the second support or to transport the x-ray tube away from the second support and the imaging device toward the second support. According to further aspects, the first support may be moveable to rotate the x-ray tube and the imaging device around a patient isocenter, wherein the treatment head is to emit treatment radiation toward the patient isocenter.

Some embodiments provide a treatment head to emit treatment radiation, a gantry coupled to the treatment head, an x-ray tube to emit imaging radiation, an imaging device to acquire an image based on the imaging radiation, and a C-arm coupled to the x-ray tube, the imaging device, and the gantry. The treatment head may emit treatment radiation toward a patient isocenter, and the C-arm may be moveable to rotate the x-ray tube and the imaging device around the patient isocenter.

Embodiments may also include emission of first imaging radiation using an x-ray tube, acquisition of a first image based on the first imaging radiation using an imaging device, emission of treatment radiation using a treatment head coupled to a gantry, and movement of a C-arm coupled to the x-ray tube, the imaging device, and the gantry. Additional aspects may include moving the C-arm to rotate the x-ray tube and the imaging device around a patient isocenter, in a case that emission of the treatment radiation comprises emitting the treatment radiation toward the patient isocenter.

In some embodiments, provided are acquisition, using a C-arm, of a three-dimensional image of a patient in a first position to receive treatment radiation, and determination of whether the first position complies with a treatment plan based on the three-dimensional image. Further, embodiments may provide delivery of the treatment radiation to the patient if it is determined that the first position complies with the treatment plan. Embodiments may also or alternatively provide acquisition of a plurality of projection images of the patient in the first position, and creation of the three-dimensional image based on the plurality of projection images.

The claims are not limited to the disclosed embodiments, however, as those skilled in the art can readily adapt the teachings herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person skilled in the art to make and use the claimed invention and sets forth the best mode contemplated by the inventors for carrying out the claimed invention. Various modifications, however, will remain readily apparent to those in the art.

Figure 1:
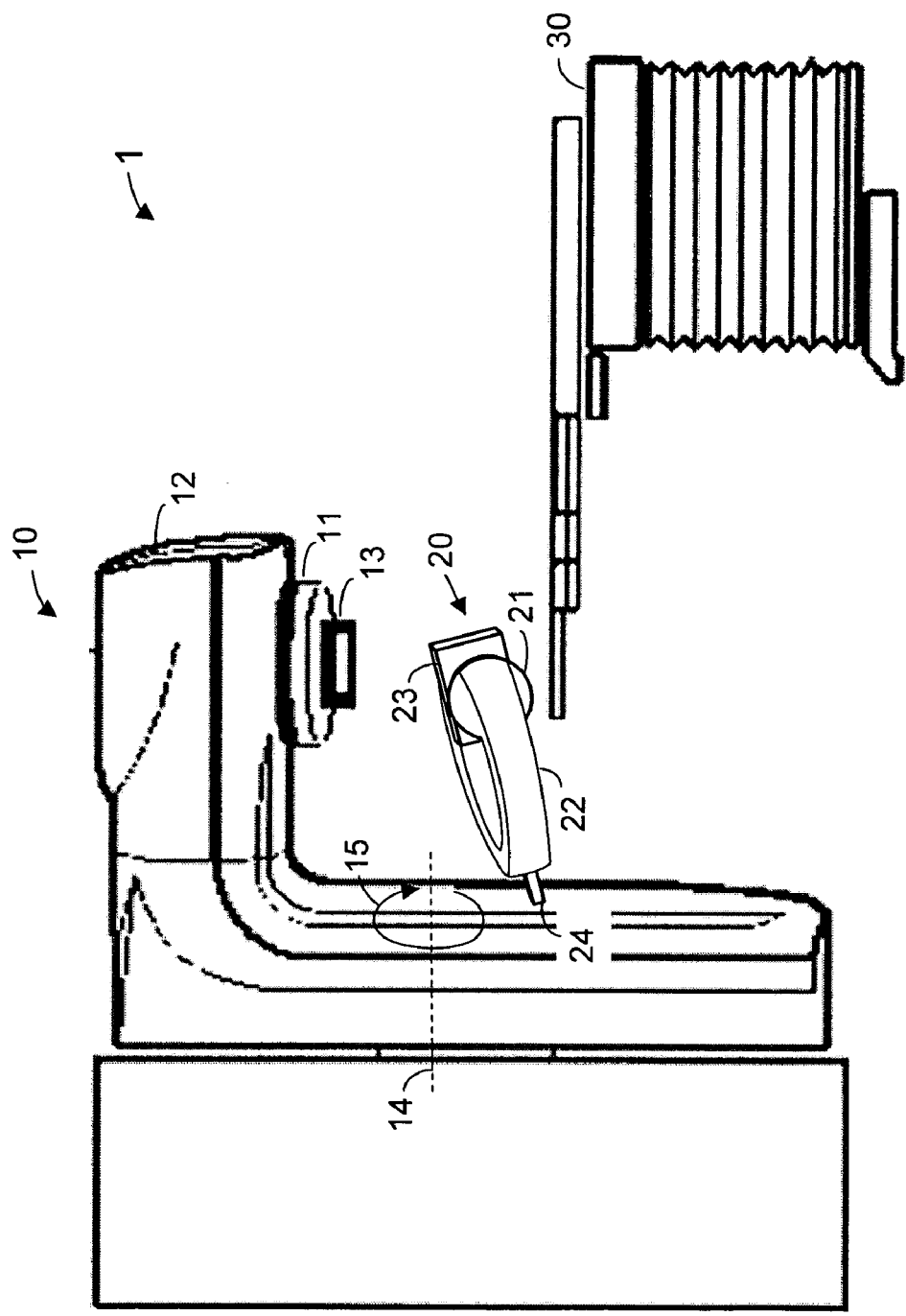
FIG. 1 is a view of a radiation treatment system according to some embodiments.

FIG. 1 illustrates radiation treatment room 1 pursuant to some embodiments. Radiation treatment room 1 includes linear accelerator (linac) 10, imaging system 20, and table 30. The elements of radiation treatment room 1 may be used to deliver treatment radiation to a patient according to a radiation treatment plan.

Linac 10 generates and emits the treatment radiation, and is primarily composed of treatment head 11 and gantry 12. Treatment head 11 includes a beam-emitting device (not shown) for emitting a radiation beam used during calibration, verification, and/or treatment. The radiation beam may comprise electron, photon or any other type of radiation. According to some embodiments, the treatment radiation comprises megavoltage radiation. Also included within treatment head 11 is a beam-shielding device, or collimator (not shown) for shaping the beam and for shielding sensitive surfaces from the beam.

Accessory tray 13 is mounted on treatment head 11 and may be configured to receive and securely hold attachments used during the course of treatment planning and treatment. These attachments may include reticles, wedges, or the like for further defining field sizes and intensities.

Treatment head 11 is fastened to a projection of gantry 12. Gantry 12 is rotatable around gantry axis 14 before, during and after radiation treatment. Although clockwise rotation is indicated by arrow 15, gantry 12 may also or alternatively rotate counter-clockwise according to some embodiments. Rotation of gantry 12 serves to rotate treatment head 11 around axis 14.

During radiation treatment, treatment radiation is delivered from linac 10 to the beam-emitting device of treatment head 11 and is emitted therefrom as a divergent beam. The beam is emitted towards a point, known as the isocenter, which may be located at the intersection of an axis of the beam and gantry axis 14. Due to divergence of the radiation beam and the shaping of the beam by the aforementioned beam-shaping devices, the beam may deliver radiation to a multi-dimensional radiation field rather than only to the isocenter.

Imaging system 20 may be used to acquire images that may be used before, during and/or after radiation treatment. For example, imaging system 20 may be used to acquire images for verification and recordation of a patient position and of an internal patient portal to which radiation is delivered. Images acquired by imaging device 20 may also be used according to some embodiments of the invention to provide three-dimensional fluoroscopy of radiation treatment.

Imaging system 20 comprises x-ray tube 21, first support 22, imaging device 23, and second support 24. X-ray tube 21 and imaging device 23 may be moveable independently of treatment head 11. According to one specific example of the foregoing, first support 22 is movable with respect to second support 24 to either transport x-ray tube 21 toward second support 24 and imaging device 23 away from second support 24, or to transport x-ray tube 21 away from second support 24 and imaging device 23 toward second support 24.

According to some embodiments, x-ray tube 21 may emit imaging radiation and imaging device 23 may acquire an image based on the imaging radiation at any point during their movement toward/away from second support 24. Imaging device 23 may therefore acquire a plurality of projection images of a body disposed between x-ray tube 21 and imaging device 23, with some of the images having different perspectives. These images may be used to create a three-dimensional cone beam reconstruction image according to currently- or hereafter-known techniques.

X-ray tube 21 may comprise any suitable device to emit imaging radiation, including but not limited to a Diabolo™ x-ray tube. In some embodiments, x-ray tube 21 emits kilovoltage radiation having energies ranging from 50 to 150 keV. Kilovoltage radiation may produce clearer images than megavoltage radiation when used in conjunction with certain imaging devices. Imaging device 23 may comprise a flat-panel imaging device using a scintillator layer and solid-state amorphous silicon photodiodes deployed in a two-dimensional array. The RID1640, offered by Perkin-Elmer®, Inc. of Fremont, Calif., is one suitable device. X-ray tube 21 and imaging device 23 may be coupled to support 22 in any suitable manner.

In operation, the scintillator layer receives x-rays and generates light in proportion to the intensity of the received x-rays. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

Imaging device 23 may comprise other types of imaging devices. For example, X-ray radiation may also be converted to and stored as electrical charge without use of a scintillator layer. In such imaging devices, x-rays are absorbed directly by an array of amorphous selenium photoconductors. The photoconductors convert the x-rays directly to stored electrical charge that comprises an acquired image of a radiation field. Imaging device 23 may also comprise a CCD or tube-based camera. Such an imaging device may include a light-proof housing within which are disposed a scintillator, a mirror, and a camera.

First support 22 may comprise any suitable structure. Support 22 may comprise a single integral element or several elements. Support 22 may include various elements for coupling itself to x-ray tube 21 and/or to imaging device 23.

Figure 2:
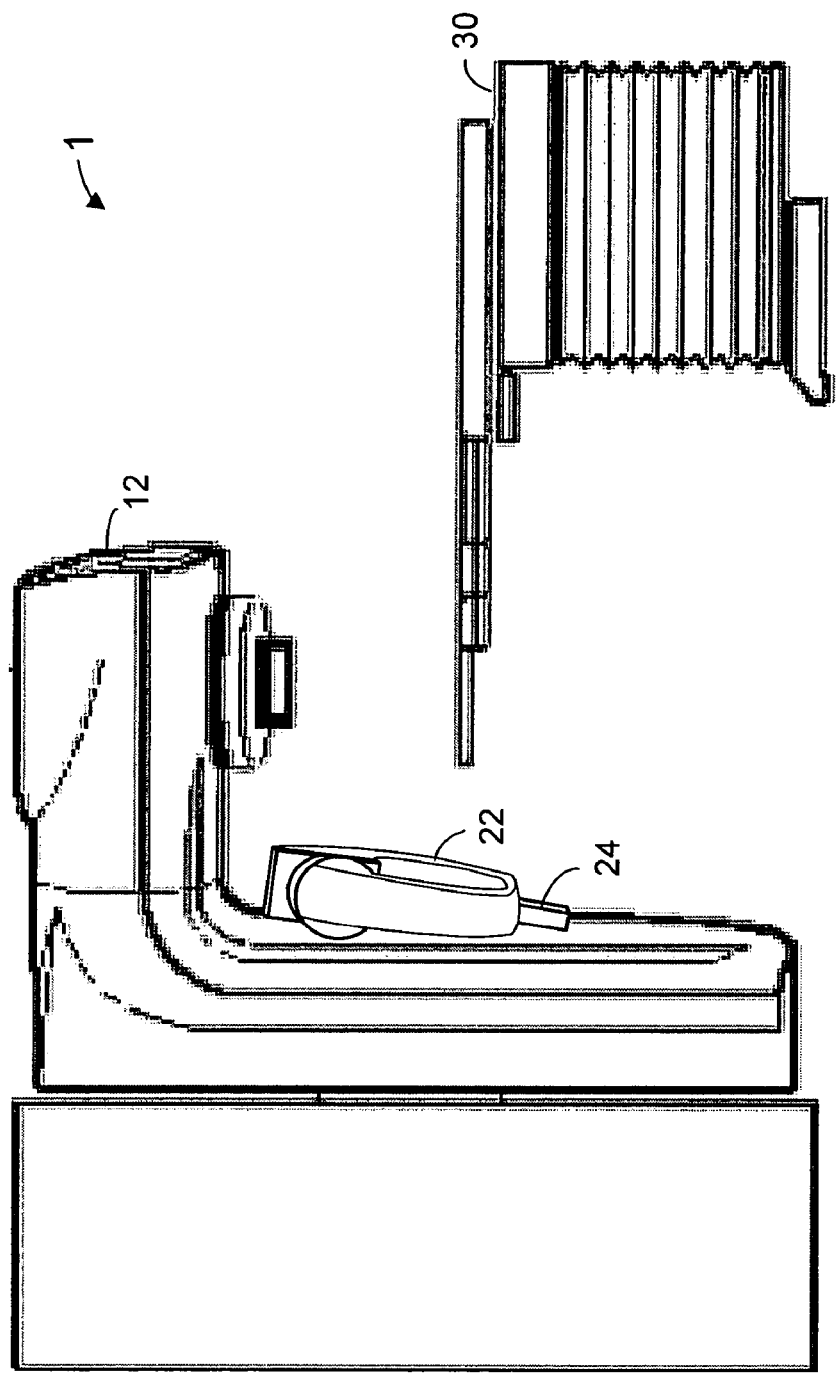
FIG. 2 is a view of a radiation treatment system according to some embodiments.

Support 22 may be slidably mounted on second support 24 and can therefore be moved in order to change the position of x-ray tube 21 and imaging device 23 with respect to treatment head 11 and with respect to table 30. Second support 24 also couples first support 22 to gantry 12. Second support 24 may be moveable to move first support 22 either toward gantry 12 or away from gantry 12. FIG. 2 illustrates system 1 after second support 24 is controlled to move first support 22 toward gantry 12. The FIG. 2 configuration may represent a "parked" position, which allows a patient to be more easily positioned on or removed from table 30.

According to some embodiments, support 22 comprises a currently- or hereafter-known "C-arm" for supporting and x-ray tube and an imaging device. Examples of C-arm-based imaging systems that may be used in conjunction with some embodiments include Siemens SIREMOBIL™, MULTI-STAR™, BICOR™ and POLYSTAR™ units, as well as other units designed to perform tomography and/or angiography. Many C-arm configurations may be used in conjunction with some embodiments of the present invention, including configurations in which second support 24 is rotatably mounted to a ceiling above linac 10, configurations in which one C-arm is slidably mounted on another C-arm, and configurations incorporating multiple independent C-arms.

Table 30 supports a patient during radiation treatment. Table 30 may be adjustable to assist in positioning a treatment area of the patient at the isocenter of linac 10. Table 30 may also be used to support devices used for calibration and/or verification.

Each of the devices shown in FIGS. 1 and 2 may include less or more elements than those shown. In addition, embodiments are not limited to the devices shown in FIGS. 1 and 2.

Figure 3:
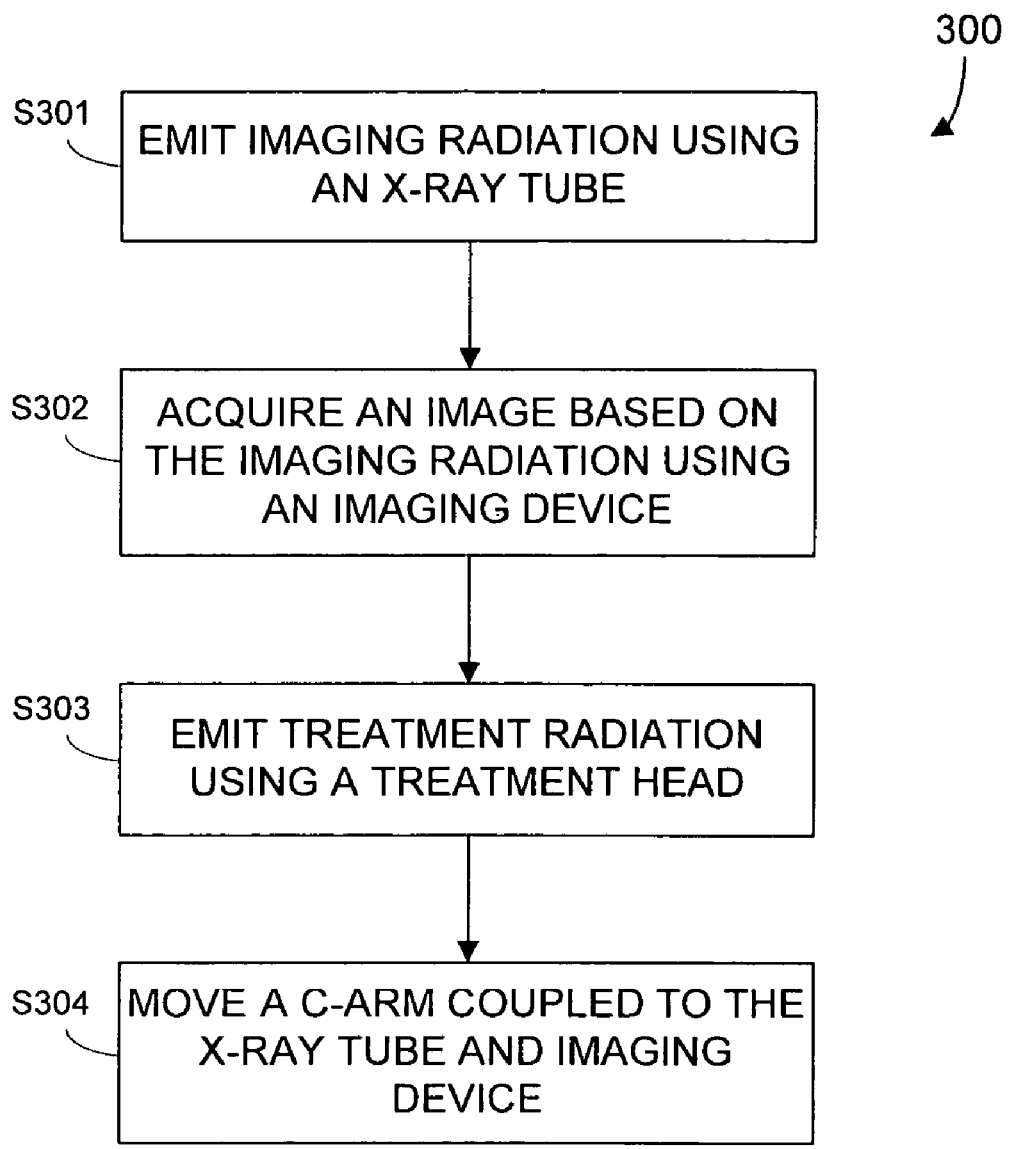
FIG. 3 is a flow diagram of process steps according to some embodiments.

FIG. 3 is a flow diagram of process steps 300 according to some embodiments. Process steps 300 may be embodied, in whole or in part, by hardware of and/or software executed by devices including but not limited to those of linac 10 and imaging system 20.

Process steps 300 may be stored by any medium, including a fixed disk, a floppy disk, a CD-ROM, a DVD-ROM, a Zip™ disk, a magnetic tape, or a signal. Some or all of process steps 300 may also be stored in one or more devices. Moreover, some or all of the process steps 300 may be implemented in hardware, such as a hardware card installed in and/or discrete circuitry of imaging system 20.

Initially, at step S301, an x-ray tube emits imaging radiation. The radiation may be emitted by x-ray tube 21 coupled to first support 22. In some embodiments, the imaging radiation is emitted toward a patient disposed in a first position. The patient may be positioned on table 30 such that a portion of the patient lies between x-ray tube 21 and imaging device 23.

An imaging device then acquires an image based on the imaging radiation in step S302. For example, imaging device 23 coupled to first support 22 may acquire an image of objects located between x-ray tube 21 and itself. More particularly, such objects may attenuate portions of the imaging radiation. Consequently, the imaging radiation received by imaging device 23 includes gradients that depend on the composition of the objects. These gradients are reflected in the acquired image and thereby represent the objects.

Next, at step S303, a treatment head such as treatment head 11 emits treatment radiation. The amount, direction, shape, and/or energy of the treatment radiation may comply with a previously-generated treatment plan. In some embodiments, the treatment radiation is emitted toward a patient disposed in the above-mentioned first position. According to some of these embodiments, the image acquired in step S302 is used prior to step S303 to verify that the position of the patient matches a position required by the treatment plan.

First support 22 is then moved in step S304. Since they are coupled to first support 22, such movement also moves X-ray tube 21 and imaging device 23. As mentioned above, the support moved in step S304 may comprise a C-arm. According to some embodiments using a C-arm, X-ray tube 21 and imaging device 23 may be moved in step S304 to either transport x-ray tube 21 toward second support 24 and imaging device 23 away from second support 24, or to transport x-ray tube 21 away from second support 24 and imaging device 23 toward second support 24.

Figure 4A:
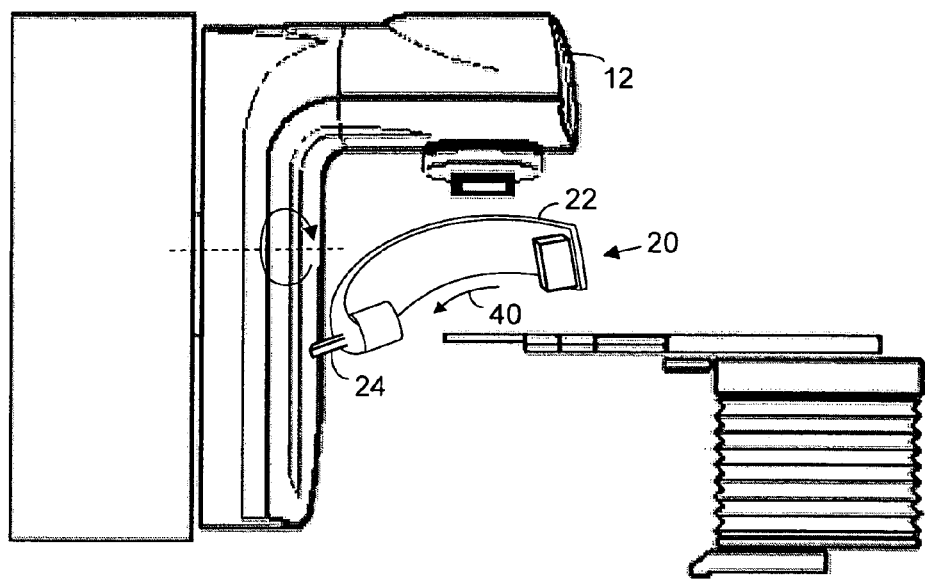
FIGS. 4A and 4B are views of a radiation treatment system in different configurations according to some embodiments.
Figure 4B:
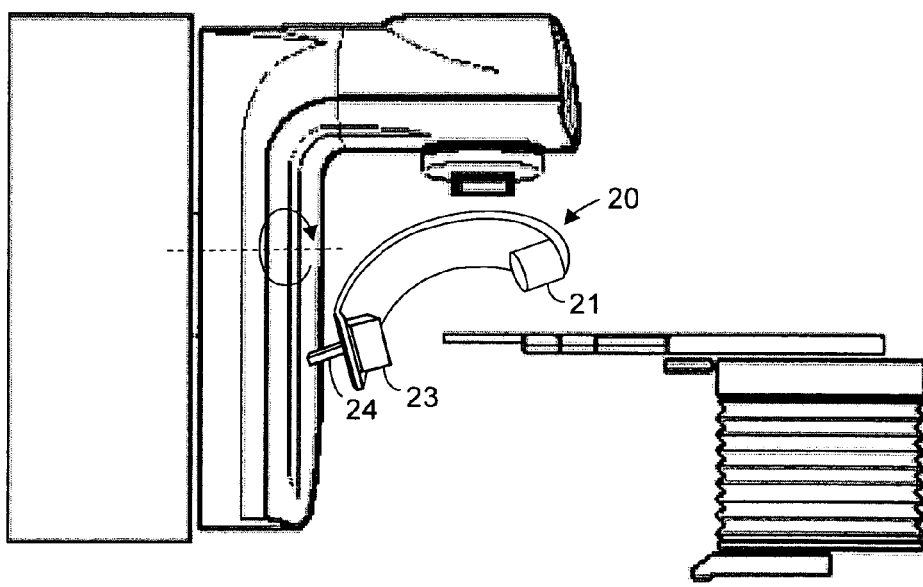

FIGS. 4A and 4B illustrate movement of first support 22 according to some embodiments. For example, it may be assumed that imaging system 20 is positioned as shown in FIG. 4A during steps S301 through S303. In this position, second support 24 positions first support 22 at substantially a 45 degree angle with respect to gantry 12.

First support 21 may then be moved in step S304 to rotate X-ray tube 21 and imaging device 23 190 degrees. Such rotation may be around a patient isocenter toward which treatment radiation is emitted in step S303. Arrow 40 indicates the direction of movement and FIG. 4B illustrates a position of imaging system 20 after completion of the movement. As shown, x-ray tube 21 has been transported away from second support 24 and imaging device 23 has been transported toward second support 24.

Flow may return to step S301 after the movement of imaging system 20 from the FIG. 4A position to the FIG. 4B position. Imaging system 20 may thereafter be used to generate another image usable to verify a position of a patient disposed on table 30.

According to some embodiments, treatment head 11 may be rotated around axis 14 at any time during process 300. In some embodiments of process steps 300, x-ray tube 21 is not coupled to gantry 12 but is also used to emit radiation towards a patient that is disposed in a position towards which treatment head 11 will emit treatment radiation. Imaging device 23 may or may not be coupled to gantry 12 according to these embodiments.

Figure 5:
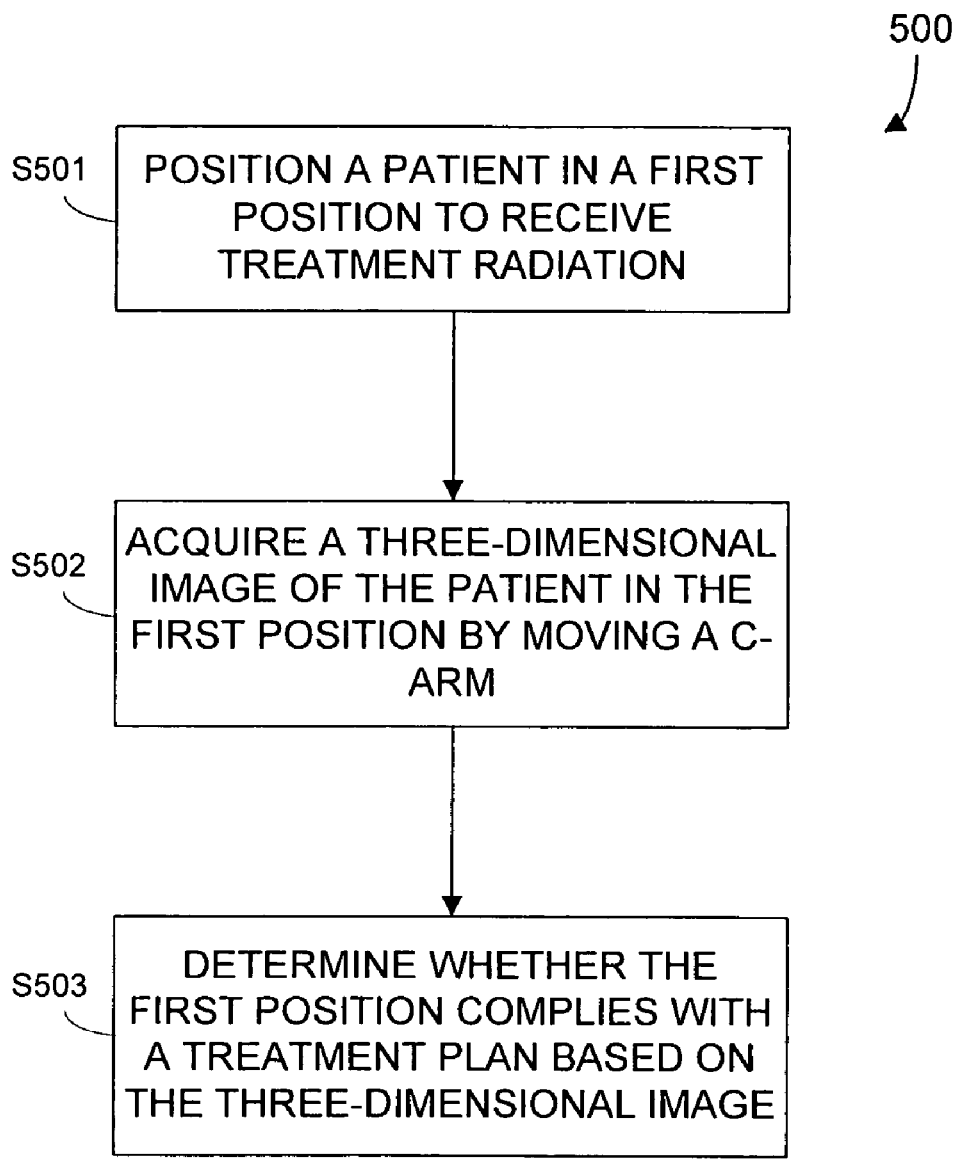
FIG. 5 is a flow diagram of process steps according to some embodiments.

FIG. 5 is a flow diagram of process steps 500 according to some embodiments. Process steps 500 may be embodied as described above with respect to process steps 300.

At step S501, a patient is positioned in a first position to receive treatment radiation. The first position may comply with a pre-established treatment plan. The patient may be positioned on table 30 using any currently- or hereafter-know patient positioning method.

A three-dimensional image of the patient is then acquired at step S502. The three-dimensional image may be acquired by moving first support 22 in order to rotate X-ray tube 21 and imaging device 23 around a region of interest such as a patient isocenter. The rotation may begin at the position shown in FIG. 4A and continue for 190 degrees around the region of interest until reaching the position of FIG. 4B.

X-ray tube 21 may emit imaging radiation and imaging device 23 may acquire a projection image based on the imaging radiation at several points along the rotation. For example, a first projection image may be acquired using imaging device 23 located at a first position relative to the patient, and a second projection image may be acquired using imaging device 23 located at a second position relative to the patient. Next, the three-dimensional image is created based on the plurality of projection images.

Based on the three-dimensional image, it is determined in step S503 whether the first position complies with a treatment plan. In one example, a processor located within system 1 determines a difference between the first position and a position required by the treatment plan by comparing an image of the planned treatment volume to the three-dimensional image. In another example, a location of a body of interest such as a tumor is confirmed using the acquired three-dimensional image. Any suitable system for determining whether the first position complies with a treatment plan may be employed in step S503. Treatment head 11 may then be used to deliver treatment radiation to the patient if it is determined that the first position complies with the treatment plan.

According to some embodiments, the patient is moved from the first position to a second position if it is determined at step S503 that the first position does not comply with the treatment plan. A second three-dimensional image of the patient in the second position may then be acquired and used to determine whether the second position complies with the treatment plan.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. An apparatus comprising:
   a treatment head to emit treatment radiation towards a patient disposed in a first position;
   an x-ray tube to emit imaging radiation towards the patient disposed in the first position;
   an imaging device to acquire an image based on the imaging radiation;
   a first support coupled to the x-ray tube and the imaging device;
   a second support, the first support slidably mounted on the second support,
   wherein the first support is movable across the second support to either transport the x-ray tube toward the second support and the imaging device away from the second support or to transport the x-ray tube away from the second support and the imaging device toward the second support; and
   a gantry coupled to the treatment head and to the second support,
   wherein the second support is moveable to move the first support either toward the gantry or away from the gantry, and the second support is moveable to create a substantially 45 degree angle between the first support and the gantry.

2. An apparatus according to claim 1, the gantry rotatable to rotate the treatment head around the patient.

3. An apparatus according to claim 1, wherein the treatment head is to emit treatment radiation toward a patient isocenter, and wherein the first support is moveable to rotate the x-ray tube and the imaging device around the patient isocenter.

4. An apparatus according to claim 3, wherein the first support is moveable across the second support to rotate the x-ray tube and the imaging device at least 190 degrees around the patient isocenter.

5. An apparatus according to claim 1, wherein the treatment head is to emit treatment radiation toward a patient isocenter, and wherein the first support is moveable to rotate the x-ray tube and the imaging device around the patient isocenter.

6. An apparatus according to claim 5, wherein the first support is moveable across the second support to rotate the x-ray tube and the imaging device at least 190 degrees around the patient isocenter.

7. An apparatus according to claim 1, the imaging device to acquire a plurality of images based on the imaging radiation, the plurality of images usable to create a three-dimensional cone beam reconstruction image.

8. A method comprising:
   emitting first imaging radiation towards a patient disposed in a first position using an x-ray tube coupled to a first support;
   acquiring a first image based on the imaging radiation using an imaging device coupled to the first support;
   emitting treatment radiation towards the patient disposed in the first position using a treatment head;
   moving the first support across a second support on which the first support is slidably mounted to either transport the x-ray tube toward the second support and the imaging device away from the second support or to transport the x-ray tube away from the second support and the imaging device toward the second support;
   rotating a pantry coupled to the treatment head to rotate the treatment head around the patient;
   moving the second support to move the first support either toward the gantry or away from the pantry; and
   moving the second support to create a substantially 45 degree angle between the first support and the gantry.

9. A method according to claim 8, wherein emitting the treatment radiation comprises emitting the treatment radiation toward a patient isocenter, and further comprising:
   moving the first support to rotate the x-ray tube and the imaging device around the patient isocenter.

10. A method according to claim 9, wherein moving the first support to rotate the x-ray tube and the imaging device comprises:
    moving the first support across the second support to rotate the x-ray tube and the imaging device at least 190 degrees around the patient isocenter.

11. A method according to claim 8, wherein emitting the treatment radiation comprises emitting the treatment radiation toward a patient isocenter, and further comprising:
    moving the first support across the second support to rotate the x-ray tube and the imaging device around the patient isocenter.

12. A method according to claim 11, wherein moving the first support to rotate the x-ray tube and the imaging device comprises:
    moving the first support across the second support to rotate the x-ray tube and the imaging device at lea 190 degrees around the patient isocenter.

13. A method according to claim 8, further comprising:
    creating a three-dimensional cone beam reconstruction image based on the first image and a second image.

14. A method according to claim 8, further comprising:
    determining whether the first position complies with a treatment plan based on the image.

15. A method according to claim 14, further comprising:
    emitting the treatment radiation towards the patient only if it is determined that the first position complies with the treatment plan.

* * * * *